United States Patent [19]
Davis et al.

[11] Patent Number: 5,660,984
[45] Date of Patent: Aug. 26, 1997

[54] DNA ISOLATING APPARATUS COMPRISING A NON-POROUS DNA BINDING, ANION EXCHANGE RESIN AND METHODS OF USE THEREOF

[76] Inventors: Thomas E. Davis, 614 Kelmore St., Half Moon Bay, Calif. 94019; Alison M. Grothe, 1327 31St. Ave., #3, San Francisco, Calif. 94122; Henry L. Schwartz, 2759 Union St., San Francisco, Calif. 94123; John Gripp, 100 Palm Ave., #4, San Francisco, Calif. 94118; Danny G. Morrow, 137 Palm Ave., San Carlos, Calif. 94070; Steven Van Huystee, 941 S. Humboldt St., San Mateo, Calif. 94402

[21] Appl. No.: 353,074

[22] Filed: Dec. 9, 1994

[51] Int. Cl.$^6$ .............................. C12Q 1/68; B01D 15/04; B01D 24/00
[52] U.S. Cl. ............................ 435/6; 435/30; 435/287.2; 435/288.6; 435/288.1; 935/19; 935/77; 210/638; 210/639; 210/641; 210/654; 210/661; 210/323.2; 210/455
[58] Field of Search ........................ 435/6, 91, 30, 435/803, 288.6, 287.2, 304.2; 536/27; 935/1, 19, 20, 21, 9, 77; 210/638, 639, 641, 654, 661, 323.2, 335, 455

[56] References Cited

U.S. PATENT DOCUMENTS

| 4,430,496 | 2/1984 | Abbott | 836/27 |
| 4,935,342 | 6/1990 | Seligson et al. | 435/6 |

FOREIGN PATENT DOCUMENTS

| 263934 | 4/1988 | European Pat. Off. | B01D 15/08 |
| 268946 | 9/1993 | European Pat. Off. | C07H 1/08 |
| 9207863 | 5/1992 | WIPO | C07H 1/08 |
| 9311218 | 6/1993 | WIPO | C12M 1/12 |

*Primary Examiner*—David A. Redding

[57] ABSTRACT

This invention relates to isolating a DNA sample from a heterogeneous mixture of the DNA and other compounds. The invention relates in particular to isolating a plasmid DNA sample from a cleared bacterial lysate. The invention provides an apparatus and method for using the apparatus to rapidly and economically isolate a DNA sample from such a mixture without the use of hazardous chemicals.

21 Claims, 2 Drawing Sheets

DNA ISOLATING APPARATUS COMPRISING A NON-POROUS DNA BINDING, ANION EXCHANGE RESIN AND METHODS OF USE THEREOF

BACKGROUND OF THE INVENTION

1. Field of the Invention

This invention relates to isolating a DNA sample from a heterogeneous mixture of DNA and other compounds. Specifically, the invention relates to isolating a DNA sample without the use of hazardous or toxic chemicals or time-consuming physical separation techniques. The invention relates in particular to isolating a plasmid DNA sample from, for example, a cleared bacterial lysate. The invention provides an apparatus and methods for using the apparatus to rapidly and economically isolate a DNA sample from such mixtures.

2. Description of the Prior Art

Modern molecular biology requires the isolation of DNA from a variety of sources comprising mixtures of the DNA with heterologous material such as proteins, lipids and other cellular constituents. Particularly important examples of such heterogeneous mixtures include cleared bacterial or yeast lysates containing plasmid or cosmid DNA, recombinant phage lysates, polymerase chain reaction mixtures, and other reaction mixtures employed in recombinant DNA methodologies. Conventional methods for separating DNA from such contaminants include extraction with a variety of organic solvents, including phenol, chloroform, and diethyl ether, followed by precipitation with ethanol, and equilibrium density centrifugation using gradients of cesium chloride, sodium chloride or sucrose. These conventional methods suffer from the disadvantages of being time-consuming and laborious, and they also involve the use of chemical reagents that are hazardous and/or toxic to the worker, the environment, or both.

Recently, it has been recognized that DNA preferentially and reversibly can be caused to bind to glass or other silicate, preferably ground glass beads, and that such bound DNA can be eluted from glass using low ionic strength buffers. This DNA binding method has lead to the of a number of commercial DNA isolation kits of a prepared slurry of glass beads and associated solutions. While advantageous for providing a commercially-available embodiment of glass-based DNA binding methods, these kits can be improved in several ways.

First, and most importantly, in the use of these kits DNA must be pelleted with the beads from solution, washed and then eluted from the beads. This mode of preparation, understood in the art as a batch mode of preparation, is disadvantageous because no provision is made for physically separating the glass beads from the eluted DNA. As a result, in the practice of these methods, it is difficult to completely remove all of the glass beads from the eluted DNA. A mixture of glass beads and a DNA sample in the final elution can compromise the accuracy of assessment of the DNA concentration and purity in the sample. The beads will continue to bind and sequester the DNA on storage, and may bind the majority of the DNA in the sample upon prolonged incubation, rendering the DNA unusable.

A second limitation of glass bead binding-based DNA isolation methods is that the glass bead binding method is a single-step procedure. It will be understood that the purity of a DNA sample, as assayed by the elimination of contaminating species such as proteins, is necessarily compromised in any single-step isolation procedure. Such single-step DNA isolation methods are known in the art, for example, methods employing the Wizard miniprep system (commercially available from Promega Corp., Madison, Wis.) and the Prep-a-Gene system (commercially available from BioRad, Inc., Hercules, Calif.). Each of these DNA isolation systems employs a single, silica-based resin in a single-step DNA purification scheme. In practice, these systems do not provide DNA having the purity required for many molecular biological procedures. Additionally, the reliability of these systems is poor in providing high-purity DNA for certain applications (e.g., fluorescent label-dependent DNA sequencing).

European Patent Application Publication No. 0263934A1, published 20 Apr. 1988 discloses the use of porous silica gel modified to have affinity ligands covalently bound to the surface of the gel particles, for DNA purification.

International Patent Application Publication No. WO93/11218, published 10 Jun. 1993, discloses methods of DNA purification comprising passing the DNA sample through a filter, the filter being characterized as having decreasing pore size in the direction of sample flow.

Another methodology used in the DNA isolation arts employs ion-exchange resins that bind to DNA, the DNA being differentially eluted from such resins using salts or other ionic competitors. Since DNA is negatively charged at all relevant pH values due to the presence of a phosphate residue between each nucleotide, it was recognized that anion exchange columns would be particularly useful for DNA sample isolations. However, anion exchange resin-based methods suffer from the drawback that anionic proteins are also bound by such anion exchange resins, and separation of DNA from such proteins is frequently impossible. In addition, elution of the DNA from such resins involves washing the resin with a salt solution, thereby requiring the eluted DNA to be purified from the salt solution by, e.g., ethanol precipitation. Ethanol precipitation can lead to loss of sample, particularly DNA samples containing small amounts of DNA or at low concentrations, and can also lead to excess salt, ethanol, or both being present in the final DNA sample. These contaminants are undesirable because they interfere with, inter alia, enzymatic manipulation of the DNA sample.

U.S. Pat. No. 5,057,426, issued Oct. 15, 1991, discloses a method for purifying a DNA sample comprising passing the DNA sample through a porous matrix that is a modified silica gel that is an anion exchange resin.

European Patent Specification, Publication No. 0268946B1, issued 15 Sep. 1993, application published 01 Jun. 1988, discloses a method for purifying a DNA sample comprising passing the DNA sample through a porous matrix that is a modified silica gel that is an anion exchange resin.

International Patent Application, Publication No. WO92/07863, published 14 May 1992, discloses a method for isolating DNA from a cell sample containing the DNA, comprising lysing the cells containing the DNA on a porous matrix, wherein the DNA is fixed on the surface of the porous matrix and then differentially eluted therefrom.

International Patent Application, Publication No. WO88/09201, published 1 Dec. 1988, discloses a device, adapted for use with a pipette, for purifying DNA from a sample.

Experimental protocols whereby these DNA isolation methods are combined are known in the prior art, but they have proven time-, labor- and material-intensive due to the perceived need to perform each DNA binding and elution step independently. An example of such a prior art recognized protocol is embodied in the Qiawell-Plus kit (commercially available from Qiagen Corp., Chatsworth, N.C.). This procedure requires two separate columns: one containing an anion exchange resin, and the other containing a silica resin. In the use of these columns, a DNA sample is first bound to the anion exchange column, washed repeatedly, then eluted from the column and the eluate recovered. The DNA sample must then be bound to the second column, washed repeatedly, and then eluted and recovered from the second column. This protocol involves disadvantageous mounts of manual manipulation of reagents, columns and DNA samples, and typically requires almost an hour of worker handling and processing to purify a DNA sample. As a result, in practice this protocol achieves only suboptimal throughput efficiencies and is time-, materials- and labor-intensive.

International Patent Application, Publication No. WO93/11221, published 10 Jun. 1993, discloses a method and apparatus for purifying nucleic acids, specifically plasmids and genomic DNA from cells, the method comprising treating the nucleic acid-containing solutions with an anion exchange resin in a low ionic strength buffer; desorbing the DNA from the anion exchange resin using a higher ionic strength buffer; treating the desorbed DNA with a mineral base in the presence of a higher ionic strength buffer or with lower alcohols/polyglycols with adsorption of the DNA onto the mineral base; and desorbing the DNA from the mineral base with water or a low ionic strength buffer.

International Patent Application, Publication No. WO93/11218, published 10 Jun. 1993, discloses methods of DNA purification comprising passing the DNA sample through a filter, the filter being characterized as having decreasing pore size in the direction of sample flow.

There is a need in the DNA isolation arts for a rapid, sensitive, and economical method of isolating DNA from a heterogeneous mixture. In particular, there is a need for combining the techniques of ion exchange chromatography and glass bead DNA binding to provide a fast, simple method of specifically isolating a DNA sample from a mixture that does not involve separation of these methodologies into two separate, unrelated, and time-consuming steps of a complicated isolation procedure.

SUMMARY OF THE INVENTION

The present invention provides an apparatus for isolating a DNA sample from a heterogeneous mixture. The apparatus comprises a column having an opening at each end. One end of the column has an opening with a diameter that is about the diameter of the column. The other end of the column is tapered and has an opening that is less than the diameter of the column. Inside the column are two solid, porous dividers, arranged so that a first divider is proximal to the open end of the column, and the second divider is proximal to the tapered end of the column. Within the column and above the dividers is an mount of a preparation of a substantially non-porous, nucleotide triphosphate-treated, copolymer of styrene and divinylbenzene having a quaternary ammonium functionality that is an anion exchange resin that comprises a first DNA binding compound. Between the dividers is an amount of a preparation of a silica gel treated with a salt, wherein the salt is selected from the group consisting of guanidine hydrochloride, guanidine isothiocyanate, hydroxylaminoguanidine, aminoguanidine hemisulfate, aminoguanidine hydrochloride, sodium chloride, lithium chloride, sodium perchlorate, sodium iodide, sodium sulfate and wherein the salt-treated silica gel is a second DNA binding compound. The salt-treated silica gel is in contact with each of the solid, porous dividers on either side, while the substantially non-porous, nucleotide triphosphate-treated, copolymer of styrene and divinylbenzene having a quaternary ammonium functionality, anion exchange resin is in contact with the first porous divider. In preferred embodiments, and oriented from the first, open end of the column, the substantially non-porous, nucleotide triphosphate-treated, anion exchange resin separated from the salt-treated silica gel by a first porous divider that is preferably a polyethylene frit. The salt-treated silica gel is in contact with each of the first and second solid, porous dividers, which each is preferably a polyethylene frit. Preferred embodiments of the porous dividers comprise polyethylene frits having an average pore size of about 1 μm. In preferred embodiments, the substantially non-porous, nucleotide triphosphate-treated, union exchange resin is treated with about 5 mM adenosine triphosphate. In preferred embodiments, the salt-treated silica gel is treated with a solution of guanidine hydrochloride at a concentration of about 5 to about 7 molar.

The present invention also includes within its scope a method for isolating a DNA sample from a heterogeneous mixture wherein the DNA sample is bound to the substantially non-porous, nucleotide triphosphate-treated, copolymer of styrene and divinylbenzene having a quaternary ammonium functionality that is an anion exchange resin, where the sample is separated from certain heterologous compounds, such as cellular components, that do not bind to this union exchange resin. The DNA sample is optionally further purified from such heterologous components by washing the column with a buffer that allows the DNA to remain preferentially bound to the substantially non-porous, nucleotide triphosphate-treated, union exchange resin. Subsequently, the DNA sample is simultaneously eluted from the substantially non-porous, nucleotide triphosphate-treated, anion exchange resin and bound to the guanidine hydrochloride-treated silica gel. The DNA is purified by washing the column with a buffer that allows the DNA to remain preferentially bound to the guanidine hydrochloride-treated silica gel, and then the DNA is eluted in substantially pure form from the column. In preferred embodiments, the sample is eluted from the substantially non-porous, nucleotide triphosphate-treated, anion exchange resin that is a copolymer of styrene and divinylbenzene having a quaternary ammonium functionality, and coincidently bound to the guanidine hydrochloride-treated silica gel using a buffer solution comprising aminoguanidine and hydroxylaminoguanidine. Most preferably, the buffer solution comprises a 50:50 mixture of aminoguanidine and hydroxylaminoguanidine. Additional advantageous buffer solutions comprise guanidine hydrochloride, guanidine isothiocyanate, hydroxylaminoguanidine hydrochloride, aminoguanidine hydrochloride, aminoguanidine hemisulfate, sodium chloride, lithium chloride, sodium perchlorate, or sodium iodide, or mixtures thereof.

The apparatus of the invention, and the methods provided for use of the apparatus for isolating a DNA sample, are advantageous over the apparatus and methods of the prior art, because the invention provides, for the first time, methods and apparatus for simultaneously utilizing ion exchange chromatography and glass bead DNA binding for isolating a DNA sample. The invention achieves this isolation by providing apparatus comprising a substantially non-porous, nucleotide triphosphate-treated, anion exchange resin that is a copolymer of styrene and divinylbenzene having a quaternary ammonium functionality, and guanidine hydrochloride-treated silica gel. The invention provides methods which allow the heterogeneous sample to be applied to the substantially non-porous, nucleotide triphosphate-treated, anion exchange resin that is separated from the guanidine hydrochloride-treated silica gel by a frit, and which methods further allow contaminating species (such as proteins, lipids and other cellular constituents) to be eluted from both the substantially non-porous, nucleotide triphosphate-treated, anion exchange resin and through the guanidine hydrochloride-treated silica gel without compromising the integrity of the silica gel to bind DNA. Importantly, the invention provides anion exchange resins that are substantially non-porous, which feature prevents binding of DNA to sites of irreversable binding. This feature also permits quantitative release of the DNA from the anion exchange resin using high ionic strength buffers comprising near-saturating amounts of certain salts, as described above, and the simultaneous binding of the DNA to guanidine hydrochloride-treated silica gel. This is achieved by providing a method that uses the same buffer to elute the DNA sample from the ion exchange resin and to bind the DNA sample to the glass beads. The invention thus advantageously provides the combination of these DNA binding compounds in a single DNA isolation column, and provides methods for combining these techniques to yield a substantially purified DNA sample.

Specific preferred embodiments of the present invention will become evident from the following more detailed description of certain preferred embodiments and the claims.

DETAILED DESCRIPTION OF THE INVENTION

Figure 1:
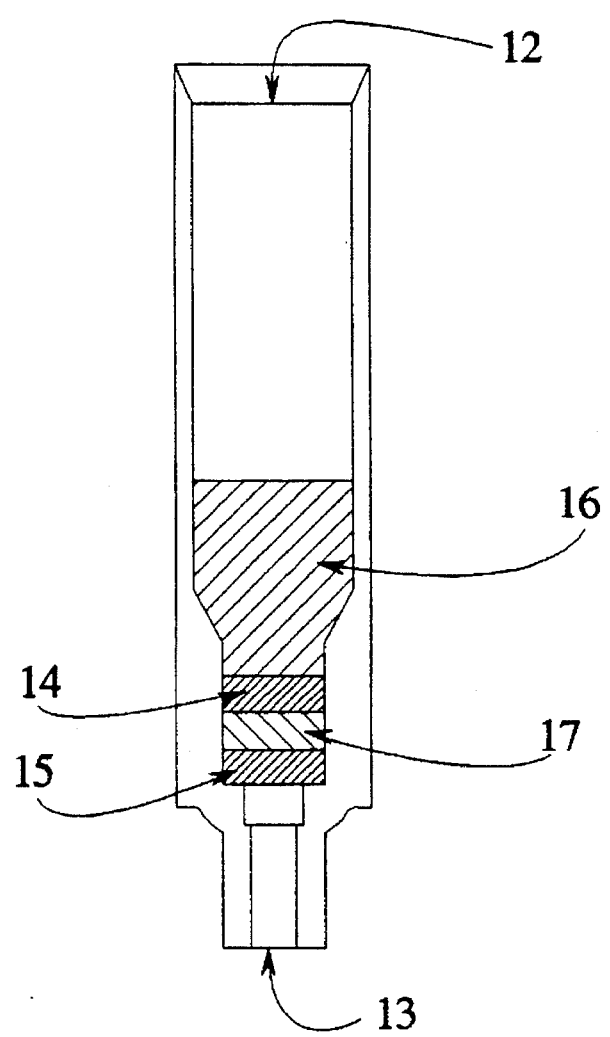
FIG. 1 is a schematic diagram of one embodiment of the DNA isolation apparatus of the invention.

The invention provides a DNA isolating apparatus. A complete understanding of the invention may be better obtained by referring to the accompanying drawings. FIG. 1 illustrates a preferred embodiment of the apparatus of the invention. In FIG. 1, there is seen a column 11 having a first opening 12 and a second, tapered end having a second opening 13, wherein the first open end has a diameter that is about the diameter of the column and the second opening at the tapered end has a diameter that is less than, preferably substantially less than, the diameter of the column. As is seen in the drawing, the second end preferably has a funnel-shaped taper leading to a columnar opening that can function as an outlet for the column. Inside the column 11 are two frits 14 and 15, arranged inside the column to delimit a portion of the interior space of the column separated by the frits. Above the first frit 14 is an amount of a preparation of a substantially non-porous, nucleotide triphosphate-treated, anion exchange resin that is a copolymer of styrene and divinylbenzene having a quaternary ammonium functionality and that is a DNA binding compound 16, and inside the space delimited by the first and second frits is an amount of a preparation of a silica gel treated with a salt, preferably guanidine hydrochloride, wherein the guanidine hydrochloride-treated silica gel is a second DNA binding compound 17. The frits and DNA binding compounds are arranged inside the column so that each of the DNA binding compounds is in contact with one or both of the frits delimiting the volume in which the DNA binding compound is contained.

The column as provided by the invention has a length that is between about 15 and 30 mm, preferably 20–30 mm, most preferably 25–28 mm and an internal diameter of between about 5–15 mm, preferably 5–10 mm, most preferably 5–7 min. The first open end of the column thus has a diameter of about 5–15 mm, preferably 5–10 mm, most preferably 5–7 mm, while the aperture at the tapered and of the column has a diameter of about 1–10 mm, preferably 1–5 mm, most preferably about 1.5–2 mm. Each of the solid porous dividers are preferably polyethylene frits that are about 1–5 mm, preferably 1–3 mm, most preferably about 1.6 mm thick and have a diameter about equal to that of the column at their position in the column. Advantageously, the polyethylene frits fit snugly within the column, making a solid contact with the column wall so that there is not enough space for particles of the first or second DNA binding compound to pass between the frit and the column wall. The polyethylene frits are characterized by apparent pore size between about 1–10 μm, preferably about 3 μm, in size. Optionally, the polyethylene frit positioned proximal to the tapered end of the column sits on a plastic or rubber O ring to provide an even more secure seal against leakage of particles of the first or second DNA binding compounds. Each of the first and second DNA binding compounds in the column are present in an amount sufficient to fill a 25–500 μL volume delimited by the polyethylene frits and the column wall. In a preferred embodiment, this apparatus is termed a Duo Column.

In one embodiment, the columns of the invention are provided individually. In other embodiments, the columns of the invention are molded into strips of 8 to 12 columns, preferably sized to accommodate a standard 96-well sample dish. Individual columns can be separated from such strips for single-sample applications. In such embodiments, the columns are preferably molded from a material that can be easily broken, including but not limited to plastics such as styrene, acrylic, polypropylene, polycarbonate, polysulfone, and the like. In other preferred embodiments, the tapered end is adapted so that a Luer-type tip can be used.

The substantially non-porous, nucleotide triphosphate-treated, anion exchange resin provided as a first DNA binding compound in the apparatus of the invention is most preferably cholestyramine as specifically provided in the formulation of cholestyramine termed Duolite and commercially available from Rohm and Haas, Philadelphia, Pa.). Cholestyramine as provided is a derivative of a copolymer of styrene and divinylbenzene having a quaternary ammonium functionality. In preferred embodiments, this cholestyramine formulation is treated to provide a substantially non-porous formulation by treatment with a solution of about 5 mM of a nucleotide triphosphate, most preferably adenosine triphosphate. Alternative nucleotide triphosphates comprise ribo-, deoxyribo and dideoxyribo-forms of such nucleotide triphosphates, and also comprise analogues, derivatives, and substituted forms of the nucleotides adenosine, guanine, cytosine and thymidine. The term "substantially non-porous" is intended to mean that, after treatment with such nucleotide triphosphate solutions, a substantial plurality of sites to which DNA molecules comprising the DNA sample to be purified would irreversably bind to the cholestyramine are blocked, thereby allowing quantitative release of the DNA sample from the cholestyramine resin upon treatment with an elution buffer, as described below. Additionally, the cholestyramine resin is mechanically sired to remove particles larger than about 12 μm in size.

The guanidine hydrochloride-treated silica gel provided as a second DNA binding compound in the apparatus of the invention is most preferably treated with a solution of guanidine hydrochloride at a concentration of about 5M to about 7M. Additional or alternative components of the treatment solution are optionally sodium chloride, sodium iodide, sodium perchlorate, lithium chloride, guanidine isothiocyanate, aminoguanidine hydrochloride, aminoguanidine hemisulfate, aminoguanidine isothiocyanate, hydroxylaminoguanidine hydrochloride, hydroxylaminoguanidine isothiocyanate, or sodium sulfate. Such alternative embodiments of the silica gel treating solution are preferably comprised of near-saturation concentrations of the salts comprising these solutions. It will be understood that the exact amounts of each salt comprising a "near-saturating solution" will depend on the exact formulation of the solution, but it will also be understood that the term "near-saturating solution" is intended to mean that the amount of any particular salt is the maximum amount of the salt that is soluble in the solution.

The guanidine hydrochloride-treated silica gel preparation that is the second DNA binding compound of the invention is provided and loaded into the DuoColumn of the invention either as a dry powder or as a slurry of the silica gel suspended in the guanidine hydrochloride solution or alternative solutions as described above. Preferably, in the loading of the DuoColumn, care is taken to prevent the guanidine hydrochloride-treated silica gel from contaminating the inside of the DuoColumn above the second porous divider, that is, the portion of the DuoColumn containing the substantially non-porous, nucleotide triphosphate-treated, anion exchange resin.

In the method of using the DNA isolating apparatus illustrated in FIG. 1, a heterogeneous mixture containing a DNA sample is applied to the column at the first, open end of the column. The column is advantageously in a substantially vertical position during application of the heterogeneous mixture, although the column may be held at an angle. The heterogeneous mixture is then passed through the column. The mixture may be applied to the column in one aliquot, or volumes of the mixture greater that the volumetric capacity of the column may be applied in several aliquots, replacing the volume applied as it is passed through the column. The mixture may be passed through the column by gravity, or the application of pressure to the first open end or a vacuum to the second, tapered end, or most preferably the mixture may be passed through the column by the action of a centripetal force placed on the column by, for example, centrifugation. In preferred embodiments, the magnitude of the centripedal force is that created by centrifugation in a desktop centrifuge or microfuge (e.g., an Eppendorf microfuge, Model #5415C, Hamburg, Germany).

After the heterogeneous mixture containing the DNA sample has been applied to the column, the DNA in the sample is bound to the substantially non-porous, nucleotide triphosphate-treated, anion exchange resin that us a copolymer of styrene and divinylbenzene having a quaternary ammonium functionality and comprises the first DNA binding compound. The amount of, for example, cholestyramine in the column is related to the amount of DNA expected to be in the heterogeneous mixture, whereby amounts of DNA and resin are optimally chosen so that the amount of DNA in the mixture does not exceed the binding capacity of the resin. The substantially non-porous, nucleotide triphosphate-treated, cholestyramine resin as provided by the invention is also characterized as having a particle size of from about 5 μm to 500 μm, preferably 5 μm to 250 μm, more preferably about 5 μm to 150 μm, and most preferably less than about 12 μm.

In the next step of the method of the invention, contaminating species that do not efficiently bind to the cholestyramine resin are washed from the column by passing the unbound heterogenous mixture through the column using gravity, pressure, an applied vacuum, or preferably by centrifugation of the column, as described above. The DNA sample remains bound to the column during this passage and is thus purified from such contaminating species. Alternatively, the column can be washed any appropriate number of times using a buffer wherein the DNA sample remains bound to the cholestyramine anion exchange resin in the column.

DNA is eluted from the cholestyramine anion exchange resin using a elution buffer under conditions wherein the DNA sample is simultaneously and quantitatively eluted from the cholestyramine anion exchange resin and bound to the guanidine hydrochloride-treated silica gel that is the second DNA binding compound of the apparatus of the invention as the elution buffer is passed through the column as described above. The elution buffer comprises a buffered solution comprising a near-saturated solution of guanidine isothiocyanate, aminoguanidine hydrochloride, aminoguanidine hemisulfate, aminoguanidine isothiocyanate, hydroxylaminoguanidine hydrochloride, hydroxylaminoguanidine isothiocyanate, or sodium sulfate. In preferred embodiments, the elution buffer comprises, 3 to 7M, and preferably 6-7M guanidine hydrochloride (GuHCl), guanidine isothiocyanate (GuSCN), or more preferably aminoguanidine hydrochloride or aminoguanidine hemisulfate or hydroxylaminoguanidine hydrochloride, most preferably a buffered solution comprising a 50:50 mixture of aminoguanidine hydrochloride and hydroxylaminoguanidine hydrochloride. Useful embodiments of the elution buffers provided by the invention also advantageously comprise a near-saturation salt solution, for example, a sodium chloride solution, preferably a 3–5M NaCl solution, or a sodium iodide, ammonium chloride, sodium perchlorate, sodium sulfate, or lithium chloride solution. It is an advantage of the most preferred embodiment of this invention if the elution buffer does not contain high concentrations of NaCl, which can interfere with recovery, activity or reactivity of the DNA and must be removed by washing, dialysis, or the like, and further that the elution buffer does not contain harmful salts of guanidine, a toxic and hazardous chemical that must be particularly neutralized before disposal into the environment.

After the DNA sample has been bound to the guanidine hydrochloride-treated silica gel, the column may be further washed to remove contaminating species from the silica, and the DNA sample purified from such contaminating species thereby. Washing is performed by applying a second washing buffer to the column and passing the buffer through the column using gravity, pressure, an applied vacuum, or preferably by centrifugation of the column. The second washing buffer preferably comprises a buffered solution containing 40–90% (v/v) ethanol. DNA bound to the silica gel is washed at least once, and preferably between one and three times with an excess of the second washing buffer; efficiency of such washes can be monitored as described above by analysis of the column eluate using conventional analytical techniques.

After the DNA bound to the silica gel has been washed, the DNA is eluted from the column. Advantageously, a fresh collection tube is positioned to collect the eluate from the tapered end of the column, preferably by placing the tapered end into the open end of the collection tube. In optional and advantageous embodiments, the outside of the column is characterized by having a uniformly raised lip which acts to stabilize the column as it is positioned into the open end of the collection tube. In preferred embodiments, the collection tube is a 1.5 mL microfuge tube, and the dimensions of the combination of the column and the microfuge tube are designed to fit inside a desktop microfuge. DNA is eluted from the column by passing an amount, preferably a minimal amount, of water or a low ionic strength buffer through the column. Useful low ionic strength buffers include, for example, TE (which is 10 mM Tris-HCl (pH 8.0)/1 mM ethylenediamine tetraacetic acid (EDTA)) and the like. The yield of recovered DNA may be determined by analysis of an aliquot of the eluted DNA using conventional techniques such as agarose or acrylamide gel electrophoresis. The apparatus and methods for using the apparatus provided by this invention are useful for isolating a DNA sample from a heterogeneous mixture. One such heterogeneous mixture comprises a plasmid DNA sample contained in a cleared bacterial lysate. Such a mixture is prepared by making bacterial spheroplasts, followed by gentle, nonionic lysis. Briefly, an amount of a bacterial culture carrying a plasmid of interest is grown in the presence of the appropriate antibiotic to select for retention of the plasmid by the bacteria. Preferred plasmids include, for example, plasmids carrying cloned, heterologous DNA (such as a portion of a eukaryotic gene) as well as an antibiotic resistance gene. After growth for a time sufficient to yield an appropriate number of bacteria (e.g., overnight growth to a density of $1 \times 10^9$ bacteria/mL), the bacteria are collected by low-speed centrifugation and resuspended in a solution containing lysozyme to digest the bacterial cell wall. After incubation to permit lysozyme-catalyzed degradation of the bacterial cell wall, the resulting bacterial protoplasts are gently lysed using any of a variety of methods. Lysis can be achieved by incubating the bacterial protoplasts in a solution containing Triton X-100 at 37°–70° C. Alternatively, the bacterial protoplasts can be lysed by heating at about 100° C. (comprising the "boiling" method) or by incubating the protoplasts in the presence of sodium hydroxide and sodium dodecyl sulfate, followed by acid precipitation of the liberated bacterial DNA and proteins (comprising the "alkaline lysis" method; each method is as described in Sambrook et al., 1990, *Molecular Cloning: A Laboratory Manual*, 2d ed., Cold Spring Harbor Laboratory Press, Cold Spring Harbor, N.Y.). Using any of the above lysis methods, the liberated bacterial DNA, lipids and cell wall proteins and other components are cleared from the solution by centrifugation, the resulting supernatant comprising the cleared lysate.

In a preferred embodiment, the DuoColunm embodiment of the invention is used to purify plasmid DNA from a cleared lysate using the following protocol. A bacterial cell pellet prepared as described above was resuspended for about 2 min in 100–200 µL of a first lysis buffer comprising lysozyme, RNase A, trehalose, EDTA and Tris-HCl (pH 8.0). After gentle mixing, the resuspended bacteria were incubated on ice for 1–10 min in this solution. Then, 100–200 µL of a second lysis buffer (comprising EDTA and Triton X-100) was added and the bacterial suspension incubated at 65° C. for about 5 minutes. The lysed bacterial suspension was centrifuged in a tabletop microfuge for about 5 min to pellet bacterial debris, and DNA was then purified from this cleared lysate using the DuoColumn.

The cleared lysate was applied to the DuoColumn and allowed to bind to the column for 4–5 min. The column was then centrifuged in a microfuge for 30 sec, and 500 µL of a first elation buffer comprising 7M guanidinium chloride was added and the column microfuged again for 30 sec. 500 µL of a wash solution (comprising 5–20 mM EDTA, 5–50 mM Tris-HCl, 2–100 mM NaCl, and 40–90% ethanol) was then added to the column and the columns were centrifuged for 5 min. The DuoColumn was then transferred to a fresh collecting tube, and 100–200 µL of a second elution buffer (comprising a solution of 10 mM Tris-HCl (pH 8.0), 1 mM EDTA) was added to the column and then centrifuged for 2 min. The purified DNA sample was collected in a volume essentially comprising the 100–200 µL of the second elution buffer applied to the column, and the quantity and quality determined using conventional procedures. The estimated total preparation time using this protocol was 35 min. Typically, yields of plasmid DNA using this protocol and the DuoColumn of the invention were found to be 15–30 µgs/mL, having a purity characterized by the ration of $A_{260}$ to $A_{280}$ of 1.7–1.8:1 (indicating about 85–90% purity).

Another example of a heterogeneous mixture from which a DNA sample may be advantageously isolated using the apparatus and methods of this invention is a polymerase chain reaction (PCR) mixture. The PCR comprises a method for amplifying in vitro a particular DNA sequence using a pair of sequence-specific primers, deoxyribonucleotides, and a polymerase such as Taq polymerase. See U.S. Pat. No. 4,683,195 to Mullis et al. and U.S. Pat. No. 4,683,202 to Mullis. The resulting mixture comprises the input template, excess unreacted single-stranded DNA primers and dNTPs, and a specific, double-stranded PCR product. Such double-stranded PCR products can be isolated for analysis or further manipulation using the apparatus and methods of the present invention.

Yet another example of a heterogeneous mixture from which a DNA sample can be advantageously isolated using the apparatus and methods of this invention is an agarose gel slice containing size-fractionated DNA, most preferably an amount of a homogenous DNA fragment. Such a gel slice can be melted at either 65° C. or 37°–50° C. (low-melting point agarose) to form a mixture of the DNA fragment(s) and the agarose. The DNA fragment comprising this DNA sample can be isolated for analysis or further manipulation using the apparatus and methods of the present invention.

It will be appreciated that additional sources of heterogeneous DNA mixtures, such as biological fluids like semen, vaginal fluids, saliva, cerebrospinal fluid, blood, urine, tears, sweat, feces, biopsy samples, and environmental and forensic samples, may be used to isolate DNA, including eukaryotic cellular DNA and DNA derived from pathological or benign microbial organisms, including bacteria, fungi, viruses, protozoans, and other microbes.

An advantageous embodiment of the apparatus of the invention is a kit comprising the column and containers containing each of the wash and elution buffers useful in using the column. The buffers provided in such kits may be either in solution or dehydrated, to be reconstituted by the addition of water by the user.

The apparatus and methods for using the apparatus to isolate a DNA sample from a heterogeneous mixture are more fully illustrated in the following Examples. These Examples illustrate certain aspects of the above-described method and advantageous results. These Examples are shown by way of illustration and not by way of limitation.

EXAMPLE 1

Preparation of a DuoColumn

A DNA isolation column apparatus was prepared as follows. Ground glass powders were prepared and sized to an average particle size of 10–40 µm using a 325 mesh screen. The glass powders were prepared from barium silicate, borosilicate, silica gel, zinc alkali silicate, alkali silicate and alumino silicate glass. In preliminary experiments, glass powders from each of these types of glass wife found to bind and elute sample DNAs equivalently; silica gel (J. T. Baker, Philadlphia, Pa.) was thereafter used in subsequent experiments. The silica gel glass powder was prepared for use by treating sequentially with 2N nitric acid, water and 7M guanidine hydrochloride. The silica was then either dried or maintained in a slurry of this salt solution. 400 µL of a slurry of silica gel glass powder was added to a plastic column prepared with one porous polyethylene frit (Porex™, Porex, Atlanta, Ga.), and a second polyethylene frit place atop the slurry. When a silica slurry was used, the slurry was loaded onto the column by placing the column, fitted with one bottom frit placed inside the column at the tapered end, onto a vacuum manifold. A measured amount (400 µL) of the slurry was fed into the column, and the silica packed in the column by drawing off the salt solution through the tapered end of the column using the vacuum manifold. When the silica bed was packed, a second polyethylene frit was placed inside the column atop and in contact with the silica bed.

Alternatively, 0.5 g of dried silica gel was loaded onto a column by first milling the dried silica to form a homogeneous powder. A vibrating turbine was used to feed the dried silica powder into a metering fixture, which was then transferred into the Duo Column.

Care was taken to avoid contaminating the inside portion of the column that would later comprise the anion exchange resin with any wet or dry amount of this guanidine hydrochloride-treated silica gel.

After loading the silica gel onto the column, a second polyethylene frit was placed inside the column atop and in contact with the silica bed.

Cholestyramine as obtained from Rohm and Haas was prepared for use by treatment with 2N acetic acid, 1–50 mM adenosine triphosphate (ATP), most preferably 5 mM ATP, and water. Typically, 100–500 μL of cholestyramine resin was added on top of the second polyethylene frit to the previously-prepared guanidine hydrochloride-treated silica gelcontaining column.

EXAMPLE 2

Plasmid DNA Purification using the DuoColumn

The plasmids pIC (Beckman, Fullerton, Calif.) and pGEM3XZf were grown in *E. coil* strain DH5α and a cleared lysate prepared for each plasmid preparation as follows. Bacteria harboring each of these plasmids were separately grown in an overnight culture at 37° C. Bacteria were pelleted from a 1–3 mL aliquot of each culture and the pellets were resuspended in 100–200 μL of a first lysis buffer containing 25% (w/v) trehalose, 40 mM EDTA, 50 mM Tris-HCl (pH 8.0), 1.25 mg/mL lysozyme and 50 μL Rnase A. After brief mixing, the resuspended bacteria were incubated for 10 min on ice, followed by the addition of 100–200 μL of a solution of 0.5M EDTA, 50 mM Tris-HCl (pH 8.0), and 0.2% (v/v) Triton X-100), and then incubated at 65° C. for 5 min. Cell debris including bacterial DNA was cleared from the lysed bacteria by centrifugation for 2–5 min, and the supernatants from each lysed bacterial sample recovered.

The cleared lysate from each culture were applied to separate DNA isolation columns, and the lysates passed through the column by centrifugation in an Eppendorf microfuge for 30 sec. Plasmid DNA was eluted from the anion exchange resin and bound to the silica gel by centrifugation through the column of 100–500 μL of an elution buffer comprising 7M GuHCl. The column was then again washed 1–3 times by centrifugation for 30 sec through the column of an excess (200–500 μL) of a washing buffer comprising 150 mM NaCl, 20 mM Tris-HCl (pH 8.0), 5 mM EDTA and 55% (v/v) ethanol.

Figure 2:
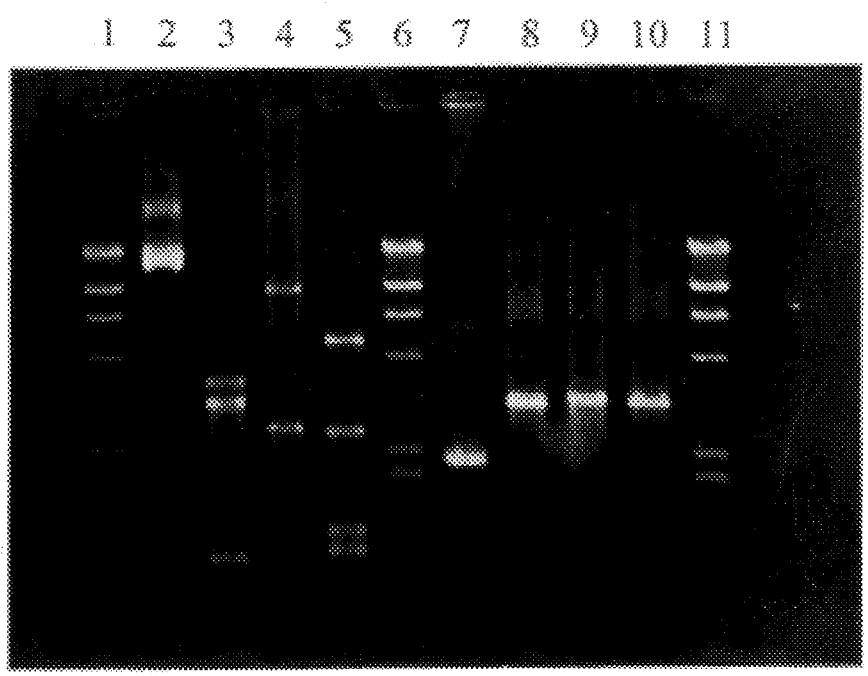
FIG. 2 is a photograph of an agarose gel containing plasmid DNAs isolated using conventional methods and the methods of the present invention.

Plasmid DNA was eluted from the columns in 100–200 μL of water. DNA recovery was analyzed by agarose gel electrophoresis, and a representative gel profile is shown in FIG. 2. Lanes 1, 6 and 11 of the gel contain DNA fragment size markers, while lanes 2 through 5 are pIC plasmid samples, and lanes 7 through 10 are pUG19 plasmid samples. Lane 2 shows the DNA profile of a 2 μL aliquot of the cleared lysate. Lanes 3, 4, and 5 each contain 200 ng of pIG as purified by the DNA isolation column of the invention as described herein, and digested with the restriction enzymes BamHI, EcoRI and HindIII, respectively. Each of these digestions produced a pattern restriction fragment that was correct and characteristic of the pIC plasmid.

Lane 7 shows the DNA profile of 2 μL of the pUC19 cleared lysate. Lane 8, 9 and 10 each contain 200 ng of pIG as purified by the DNA isolation column of the invention as described herein, and digested with the restriction enzymes BamHI, EcoRI and HindIII, respectively. Each of these digestions produced a pattern restriction fragment that was correct and characteristic of the pGEM plasmid.

These results demonstrate that high purity DNA can be isolated from a cleared bacterial lysate quickly and efficiently using the DuoColumn and methods of the invention, and that plasmid so purified is competent for routine molecular biological manipulations.

It should be understood that the foregoing disclosure emphasizes certain specific embodiments of the invention and that all modifications or alternatives equivalent thereto are within the spirit and scope of the invention as set forth in the appended claims.

What is claimed is:

1. A apparatus for isolating a DNA sample from a heterogeneous mixture, comprising a column having a first end and a second end, wherein the first end forms an opening having a diameter substantially equal to the interior diameter of the column and the second end is tapered to form an aperture having an interior diameter less than diameter of the opening at the first end, the apparatus further comprising a first and a second solid porous divider, an amount of a preparation of a substantially non-porous, nucleotide triphosphate-treated, anion exchange resin that is a copolymer of styrene and divinylbenzene having a quaternary ammonium functionality and that comprises a first DNA binding compound, and an amount of a preparation of a guanidine hydrochloride-treated silica gel that is a second DNA binding compound, wherein the first porous divider is proximal to the first open end of the column, and the second porous divider is proximal to the second, tapered end of the column, and wherein an amount of the substantially non-porous, nucleotide triphosphate-treated anion exchange resin is contained in the column and above the first divider and operably in contact with the first divider, and an amount of the guanidine hydrochloride-treated silica gel is between the first and second divider and operably in contact with both dividers.

2. The apparatus of claim 1 wherein the solid porous dividers comprise a porous frit or membrane.

3. The apparatus of claim 1 wherein the substantially non-porous, adenosine triphosphate-treated, anion exchange resin is treated with a solution comprising about 5 mM adenosine triphosphate.

4. The apparatus of claim 1 wherein the guanidine hydrochloride-treated silica gel is treated with a solution comprising about 5M to about 7M guanidine hydrochloride.

5. A method of isolating a DNA sample from a heterogeneous mixture, comprising the steps of:
   (a) applying the heterogeneous mixture to the apparatus of claim 1 at the first open end of the apparatus;
   (b) passing the heterogeneous mixture through the apparatus and binding the DNA sample to the substantially non-porous, adenosine triphosphate-treated, anion exchange resin that is copolymer of styrene and divinylbenzene having a quaternary ammonium functionality;
   (c) simultaneously eluting the DNA sample from the substantially non-porous, nucleotide triphosphate-treated, anion exchange resin and binding the DNA sample to the guanidine hydrochloride-treated silica gel by passing a first elution buffer through the apparatus, wherein the first elution buffer is a high ionic strength buffer comprising a near-saturation concentration of a chaotropic agent selected from the group consisting of diamineimine, ketoaminimine, hydroxyamineimine, aminiguanidine hydrochloride, aminoguanidine hemisulfate, hydroxylaminoguanidine hydrochloride, guanidine hydrochloride, guanidine isothiocyanate, and mixtures thereof;
   (d) washing the DNA sample bound to the guanidine hydrochloride-treated silica gel by passing an amount of a washing buffer through the apparatus; and
   (e) eluting the DNA sample from the guanidine hydrochloride-treated silica gel with a second elution solution comprising water or a low ionic strength buffer solution.

6. The method of claim 5 wherein the elution buffer comprises a solution comprising a 50:50 mixture of aminoguanidine and hydroxylaminoguanidine.

7. The method of claim 5 wherein the elution buffer also comprises a near-saturated solution of a salt selected from the group consisting of sodium chloride, sodium iodine, sodium perchlorate, lithium chloride, and mixtures thereof.

8. The method of claim 5 wherein the heterogeneous mixture is a cleared bacterial lysate.

9. The method of claim 5 wherein the heterogeneous mixture is a yeast lysate.

10. The method of claim 5 wherein the heterogeneous mixture is a polymerase chain reaction mixture.

11. The method of claim 5 wherein the heterogeneous mixture is a melted agarose gel slice.

12. A method of isolating a DNA sample from a heterogeneous mixture, comprising the steps of:

(a) applying the heterogeneous mixture to the apparatus of claim 1 at the first open end of the apparatus;

(b) passing the heterogeneous mixture through the apparatus and binding the DNA sample to the substantially non-porous, nucleotide triphosphate-treated, anion exchange resin that is a copolymer of styrene and divinylbenzene having a quaternary ammonium functionality;

(c) washing the DNA sample bound to the substantially non-porous, nucleotide triphosphate-treated, anion exchange resin by passing an amount of a first washing buffer through the apparatus;

(d) simultaneously eluting the DNA sample from the substantially non-porous, nucleotide triphosphate-treated, anion exchange resin and binding the DNA sample to the guanidine hydrochloride-treated silica gel by passing a first elution buffer through the apparatus, wherein the first elution buffer is a high ionic strength buffer comprising a near-saturation concentration of a chaotropic agent selected from the group consisting of diamineimine, ketoaminimine, hydroxyamineimine, aminiguanidine hydrochloride, aminoguanidine hemisulfate, hydroxylaminoguanidine hydrochloride, guanidine hydrochloride, guanidine isothiocyanate, and mixtures thereof;

(e) washing the DNA sample bound to the guanidine hydrochloride-treated silica gel by passing an amount of a washing buffer through the apparatus; and (f) eluting the DNA sample from the guanidine hydrochloride-treated silica gel with a second elution solution comprising water or a low ionic strength buffer solution.

13. The method of claim 12 wherein the elution buffer comprises a solution comprising a 50:50 mixture of aminoguanidine and hydroxylaminoguanidine.

14. The method of claim 12 wherein the elution buffer also comprises a near-saturated solution of a salt selected from the group consisting of sodium chloride, sodium iodine, sodium perchlorate, lithium chloride, sodium sulfate, and mixtures thereof.

15. The method of claim 12 wherein the heterogeneous mixture is a cleared bacterial lysate.

16. The method of claim 12 wherein the heterogeneous mixture is a yeast lysate.

17. The method of claim 12 wherein the heterogeneous mixture is a polymerase chain reaction mixture.

18. The method of claim 12 wherein the heterogeneous mixture is a melted agarose gel slice.

19. An article of manufacture comprising a kit for isolating a DNA sample from a heterogeneous mixture, the kit comprising in combination:

(a) the apparatus of claim 1;

(b) a first container comprising a first lysis buffer;

(c) a second container comprising a second lysis buffer;

(d) a third container comprising a first elution buffer;

(e) a fourth container comprising a washing buffer; and (f) a fifth container comprising a final elution buffer.

20. The article of manufacture of claim 19 wherein each of the buffers are provided in a dry state.

21. A apparatus for isolating a DNA sample from a heterogeneous mixture, comprising a column having a first end and a second end, wherein the first end forms an opening having a diameter substantially equal to the interior diameter of the column and the second end is tapered to form an aperture having an interior diameter less than diameter of the opening at the first end, the apparatus further comprising a first and a second solid porous divider, an amount of a preparation of a substantially non-porous, nucleotide triphosphate-treated, cholestyramine anion exchange resin that comprises a first DNA binding compound, and an amount of a preparation of a silica gel treated with a salt, wherein the salt is selected from the group consisting of guanidine hydrochloride, guanidine isothiocyanate, hydroxylaminoguanidine hydrochloride, aminoguanidine hemisulfate, sodium chloride, lithium chloride, sodium perchlorate, and sodium iodide, and wherein the salt-treated silica gel is a second DNA binding compound, wherein the first porous divider is proximal to the first open end of the column, and the second porous divider is proximal to the second, tapered end of the column, and wherein an amount of the substantially non-porous cholestyramine anion exchange resin is contained in the column and above the first divider and operably in contact with the first divider, and an amount of the silica gel is between the first and second divider and operably in contact with both dividers.

* * * * *